United States Patent [19]

Richeson

[11] Patent Number: 4,576,164
[45] Date of Patent: Mar. 18, 1986

[54] KNIFE WITH LOCKING SHROUD

[76] Inventor: W. George Richeson, 182 Mountain Brook Dr. NW., Marietta, Ga. 30064

[21] Appl. No.: 551,344

[22] Filed: Nov. 14, 1983

[51] Int. Cl.⁴ ............................................. A61B 17/32
[52] U.S. Cl. ...................................... 128/305; 30/162
[58] Field of Search ........................ 128/305; 401/117; 30/151, 162, 293

[56] References Cited

U.S. PATENT DOCUMENTS 928,312  7/1909  Lloyd ................................. 401/117
4,414,974 11/1983 Dotson et al. ....................... 128/305

Primary Examiner—Hugh R. Chamblee
Attorney, Agent, or Firm—James B. Middleton

[57] ABSTRACT

A microsurgical knife having a shroud that can be locked in two or three positions. The knife has a body with a blade at one end, and an enlarged cap at the other, the cap acting as a stop for the shroud. Grooves along the knife body receive projections on the shroud allowing the shroud to slide but not rotate. Locking grooves extend circumferentially from the grooves so the shroud can be rotated to place a projection in a locking groove and prevent inadvertent longitudinal movement of the shroud. Locking grooves are placed so the shroud can be placed in blade covering position, in the extreme rearward position, and in an intermediate position wherein the shroud acts as an enlarged centrally located handle.

4 Claims, 4 Drawing Figures

U.S. Patent  Mar. 18, 1986  4,576,164
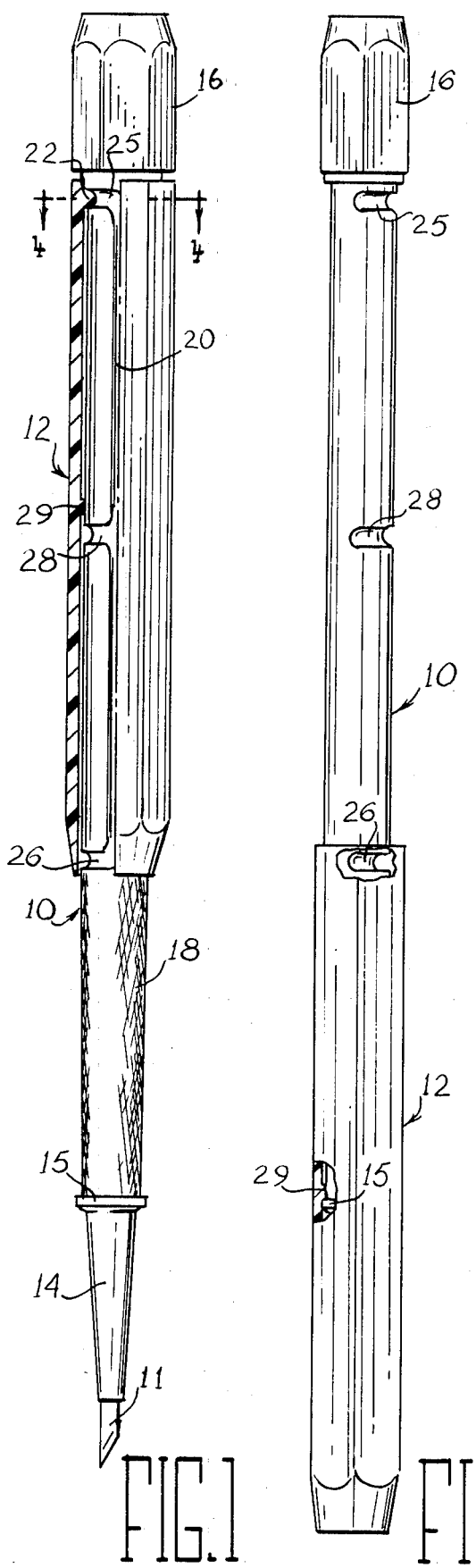
FIG.1
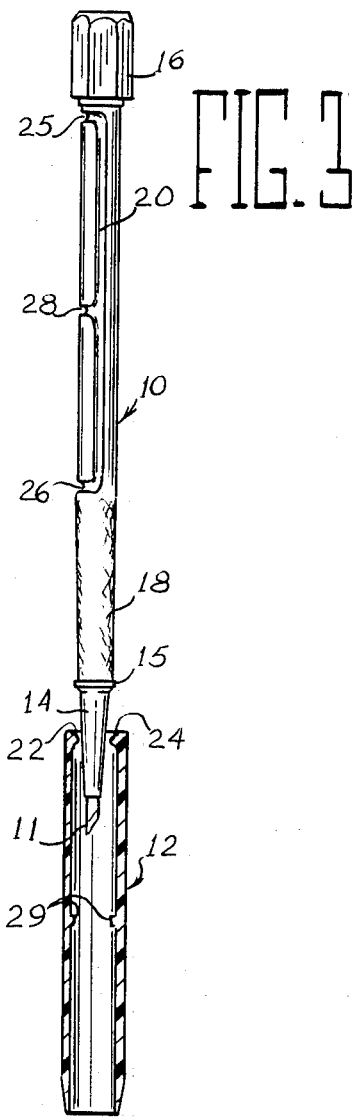
FIG.2
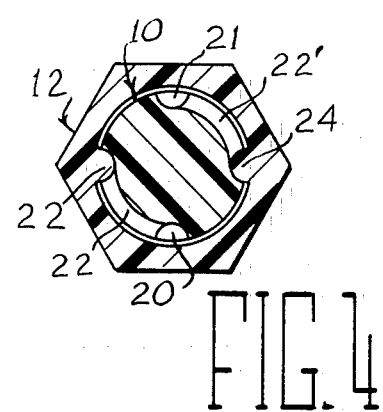
FIG.3
FIG.4

KNIFE WITH LOCKING SHROUD

INFORMATION DISCLOSURE STATEMENT

Various forms of cutting implements having coverings or shrouds are well known in the art. The most common use of a shroud or the like is to allow a knife or other implement to be put into one's pocket without danger of cutting clothing. More recently, there has been a disposable microsurgical knife for use in ophthalmic and other microsurgical procedures wherein the knife has a slidable shroud to allow the extremely sharp cutting blade to be covered for packaging and shipping, as well as for passing between the surgeon and an assistant in the operating room. This knife is disclosed in U.S. Pat. No. 4,414,974 issued Nov. 15, 1983, to Dotson et al.

It will be understood by those skilled in the art that the microsurgical knife is rather small and lightweight. The body of the knife is shaped for maximum visibility of the operating site which of course requires a relatively small diameter body. The sliding shroud on the prior art knife will serve to shield the cutting blade; however, the shroud tends to be readily slidable, and sometimes slides inadvertently. Also, the ready slidability of the shroud militates against some of the attempted used of the knife.

SUMMARY OF THE INVENTION

This invention relates generally to surgical knives, and is more particularly concerned with a disposable microsurgical knife having a selectively slidable shroud.

The present invention provides a disposable microsurgical knife having a selectively movable shroud, the shroud being movable axially of the knife body, with locking means for selectively locking the shroud in a selected position. The shroud is in the form of a sleeve that is movable along the knife body, the sleeve being disposable in a forward position wherein the knife blade is within the confines of the sleeve, and the sleeve is further disposable in at least one rearward position wherein the knife blade is exposed for use. Preferably, a plurality of locking means is provided so the shroud or sleeve can be locked in the blade covering position, and in at least one blade using position. The present invention therefore provides a microsurgical knife that is easy to manipulate, and includes an effective protective shroud usable both to cover the knife blade and to provide a convenient grip for a surgeon.

BRIEF DESCRIPTION OF THE DRAWINGS

These and other features and advantages of the present invention will become apparent from consideration of the following specifications when taken in conjunction with the accompanying drawings in which:

FIG. 1 is a side elevational view of a knife made in accordance with the present invention, the shroud being shown partially in cross-section, and in the rearmost position;

FIG. 2 is an elevational view similar to FIG. 1 with the shroud shown in blade protecting position and the knife rotated 90° from the position shown in FIG. 1;

FIG. 3 is a side elevational view showing the shroud in position for initial assembly of the shroud and the knife body; and, FIG. 4 is an enlarged cross-sectional view taken substantially along the line 4—4 in FIG. 1.

DETAILED DESCRIPTION OF THE EMBODIMENT

Referring now more particularly to the drawings, and to that embodiment of the invention here presented by way of illustration, in FIG. 1 it will be seen that the microsurgical knife includes generally a knife body 10 having a cutting blade 11 at one end thereof. The shroud designated at 12 is slidable along the knife body 10, and is shown in its rearmost position.

In more detail, it will be seen that the knife body 10 includes a forward portion 14 that tapers downwardly towards the blade 11 to provide good visibility of the cutting tip of the knife. Rearwardly of the forward portion 14, there is a ring 15 for centering the shroud 12. This structure is disclosed in the above identified patent to Dotson et al., the disclosure of which is incorporated herein by reference.

At the rearmost end of the knife body 10, there is a cap 16. For aesthetic purposes, the exterior configuration of the cap 16 is preferably the same as the exterior configuration of the shroud 12. Though it will be understood that any shape may be utilized, the purpose of the cap 16 is to provide a definite limit to the rearward motion of the shroud 12.

Between the ring 15 and the cap 16, the body 10 has a gripping portion 18 that may be knurled or otherwise roughened to provide a secure grip. Also, the gripping portion 18 is somewhat frusto-conical, having the smaller diameter adjacent to the ring 15.

From the foregoing, it will now be seen that the knife as shown in FIG. 1 is in condition for use, with the blade 11 exposed. In this condition, the forward tip is reduced in size for good visibility of the blade area, and the knife continues to taper, including the gripping portion 18 that is knurled for providing a good grip. Finally, the shroud 12 provides an enlarged portion to be conveniently held. It will also be seen that the shroud 12 is noncircular in configuration, and is preferably formed as a polygon.

With the foregoing discussion in mind, it will be understood that, when the shroud 12 is in the forwardmost position as shown in FIG. 2 of the drawings, it is generally desirable to prevent inadvertent motion of the shroud. One of the advantages of the shroud for covering the knife blade 11 is that relatively simple packaging can be used for the disposable knives, and the blades will not be damaged in shipping because of the protection by the shroud 12. It has been found with the prior art knives that the shroud will sometimes move rearwardly to expose the knife blade and allow the blade to be damaged. Also, it has been found that, when in use, the shroud will sometimes move from its intended position.

A distinct disadvantage of the prior art disposable microsurgical knife is that tolerances must be maintained rather close because the shroud is intended to stay in its rearward position due to a wedging effect between the shroud and the body of the knife. Similarly, the shroud was intended to stay in its blade covering position simply by a wedging effect. In practice, it was found that the tolerances were difficult to maintain, resulting in a large percentage of rejects.

Due to the small size, and the general configuration of the knife, some surgeons prefer to use the shroud 12 in an intermediate position, feeling that control of the knife is enhanced by the appropriate position of the shroud. With the prior art knives, of course, the shroud was slidable and such use was not always successful.

With the foregoing in mind, it will be seen that the knife of the present invention includes a pair of longitudinally extending grooves 20 and 21. The grooves 20 and 21 extend from a point just below the cap 16 to a point just above the forward gripping portion 18. As here illustrated, the grooves 20 and 21 are diametrically opposed, extending parallel to each other on opposite sides of the knife body 10.

Cooperating with the grooves 20 and 21, the shroud 12 has a pair of projections 22 and 24. The projections 22 and 24 are located substantially adjacent to the rearmost end of the shroud 12, though the exact dimensions of the individual knife will determine the precise location of the projections 22 and 24.

With the projections 22 and 24 running in the grooves 20 and 21, it will be understood that the shroud 12 can move axially of the body 10 of the knife, and the shroud 12 will not rotate with respect to the body 10. To provide a locking means for the shroud 12, locking grooves are extended circumferentially of the knife body, in communication with the grooves 20 and 21. As shown in the drawings, the embodiment of the invention here presented includes three locking grooves designated at 25, 26 and 28 extending from the groove 20. The locking grooves extending from the groove 21 are designated at 25', 26' and 28'. The locking grooves blend smoothly with the longitudinal grooves 20 and 21 so the projections 22 and 24 can slip smoothly into the various locking grooves.

It will now be seen that the shroud 12 can be placed in its rearmost position as shown in FIG. 1, and the projections 22 and 24 can be received within the locking grooves 25 and 25'. When the shroud is to be moved to a different position, the shroud 12 can be rotated approximately 90° with respect to the knife body 10, and the projections 22 and 24 will ride in the longitudinal grooves 20 and 21 allowing the shroud 12 to be moved to the desired position. When the shroud 12 is to be placed in the blade protecting position as shown in FIG. 2, the projections 22 and 24 can move into the locking groove 26 and 26' by a simple rotation of the shroud 12 with respect to the knife body 10. Also, in the event a surgeon wishes to use the knife with the shroud 12 in the intermediate position so the shroud 12 acts as a handle, the projections 22 and 24 can extend into the locking grooves 28 and 28'. In this position, the shroud 12 can be used as the handle of the knife, and the shroud 12 will not inadvertently slip from the desired position. It will be obvious to those skilled in the art that the entrance to the locking grooves can be made slightly restricted so a more definite effort is required to move the projections 22 and 24 into or out of the various locking grooves.

With attention to FIG. 3 of the drawings, it will be understood that the shroud 12 and the knife body 10 will generally be molded as separate pieces, and the two pieces later assembled. It will be seen that the ring 15 has a tapered forward side, and the projections 22 and 24 are here shown as generally hemispherical. With this combination, the shroud 12 can be slipped over the ring 15, and the normal yieldability of the plastic material will allow the shroud 12 to be slipped onto the body 10 until the projections 22 and 24 are received in the grooves, such as the grooves 26 and 26'.

It will also be seen in FIGS. 2 and 3 of the drawings that the shroud 12 includes a plurality of projections 29. These projections 29 will also ride over the ring 15 for purposes of assembly; however, the rear side of the ring 15 is generally straight so the projections 29 will not easily slip over the ring. This is a further stop means to prevent the shroud from coming completely off the knife body, and it will be seen that the ring 15 maintains the shroud 12 centered on the knife body 10. It is contemplated that, when the shroud 12 is in the intermediate position with the projections 22 and 24 and the locking grooves 28 and 28', the shroud 12 will engage the ring 15 so the knife body 10 will not move radially of the shroud 12. This provides a stable knife body that is accurately useable by the surgeon.

It will of course be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as defined in the appended claims.

I claim:

1. A microsurgical knife, said knife including an elongate knife body, a cutting blade extending from one end of said knife body, and a selectively slidable shroud received over said knife body, said shroud defining a generally cylindrical bore therethrough for receiving said elongate body, said knife body defining a longitudinal groove therein, a projection carried by said shroud and slidably receivable within said longitudinal groove, said projection being located within said bore and projecting radially thereof, said longitudinal groove extending along said knife body parallel to the axis of said knife body, said body further including a cap at the end of said knife body opposite said one end, said cap being sufficiently large to prevent movement of said shroud beyond said cap, said body further defining a first locking groove extending circumferentially of said knife body and communicating with said longitudinal groove, said first locking groove being located so that, when said shroud is in a first position surrounding said cutting blade, said projection is receivable within said first locking groove by rotation of said shroud with respect to said knife body, a second locking groove extending circumferentially of said knife body and communicating with said longitudinal groove, said second locking groove being located so that, when said shroud is in a second position exposing said cutting blade and adjacent to said cap, said projection is receivable within said second locking groove by rotation of said shroud with respect to said knife body, and a third locking groove extending circumferentially of said knife body and communicating with said longitudinal groove, said third locking groove being located so that, when said shroud is in a third position exposing said cutting blade with said shroud in an intermediate position on said knife body, said projection is receivable within said third locking groove by rotation of said shroud with respect to said knife body, said knife body being tapered towards said one end, said knife body including a ring for centering said shroud on said knife body when said shroud is in said first position.

2. A microsurgical knife as claimed in claim 1, said knife body and said shroud being formed of a plastic material, said ring including a sloped side towards said one end of said knife body for allowing said projections to ride over said ring for assembly of said knife, said shroud further including intermediate projections extending inwardly of said bore, said intermediate projections being located such that said intermediate projections are adjacent to said ring when said shroud is in said first position.

3. A microsurgical knife as claimed in claim 1, said knife body further defining a second longitudinal groove therein; said second longitudinal groove being located opposite said longitudinal groove and disposed parallel thereto, a second projection carried by said shroud opposite said projection and slidably received in said second longitudinal groove.

4. A microsurgical knife as claimed in claim 3, and further including a second plurality of locking grooves, each locking groove of said second plurality of locking grooves being located opposite one of said first, second and third locking grooves and in communication with said second longitudinal groove.

* * * * *